US006544543B1

(12) United States Patent
Mandrusov et al.

(10) Patent No.: US 6,544,543 B1
(45) Date of Patent: Apr. 8, 2003

(54) PERIODIC CONSTRICTION OF VESSELS TO TREAT ISCHEMIC TISSUE

(75) Inventors: Evgenia Mandrusov, Campbell, CA (US); Christopher J. Buchko, Redwood City, CA (US); Wouter E. Roorda, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/752,399

(22) Filed: Dec. 27, 2000

(51) Int. Cl.$^7$ .............................. A61F 13/00; A61F 2/06
(52) U.S. Cl. ........................ 424/422; 424/423; 424/489
(58) Field of Search ................................ 424/422, 423, 424/489

(56) References Cited

U.S. PATENT DOCUMENTS

| | | | |
|---|---|---|---|
| 5,464,650 A | 11/1995 | Berg et al. | 427/2.3 |
| 5,542,935 A | 8/1996 | Unger et al. | 604/190 |
| 5,580,575 A | 12/1996 | Unger et al. | 424/450 |
| 5,605,696 A | 2/1997 | Eury et al. | 424/423 |
| 5,652,059 A | 7/1997 | Margel | 428/403 |
| 5,749,915 A | 5/1998 | Slepian | 623/1 |
| 5,749,922 A | 5/1998 | Slepian et al. | 623/1 |
| 5,770,222 A | 6/1998 | Unger et al. | 424/450 |

OTHER PUBLICATIONS

Weihrauch et al., "Repetitive coronary artery occlusions induce release of growth factors into myocardial interstitium", Am. J. Physiol., 275 (3 pt 2): H969–76 (1998).*
Tahara et al., "Vasopressin increases vascular endothelial growth factor secretion from human vascular smooth muscle cells", Eur J Pharmacol, 26;368 (1): 89–94 (1999).*
Hupf, et al., "Evidence for a vasopressin system in the rat heart", Circulation Research, 84 (3):365–70 (1999).*
Boillet et al., "Effects of propofol on vascular reactivity in isolated aortae from normotensive and spontaneously hypertensive rats", British Journal of Anaesthesia, (1999) 83 (4): 622–9.
Buschmann et al., "Arteriogenesis Versus Angiogenesis: Two Mechanisms of Vessel Growth", News Physiol. Sci., Jun., 1999, vol. 14: 121–125.
Chilian et al., "Microvascular occlusions promote coronary collateral growth", The American Physiological Society, (1990) H1108–H1111.
Kersten et al., "Modulation of Coronary Collateral Angiogenesis: A Canine Model of Neovascularization Induced by Chronic Ischemia", J. Card. Surg., (1995) 10:354–357.
Klibanov et al., "Targeting of Ultrasound Contrast Material", Acta Radiologica 38, (1997) Supplement 412, 113–120.
Loichot et al., "Nitric oxide, but not vasopressin $V_2$ receptor-mediated vasodilation, modulates vasopressin–induced renal vasoconstriction in rats", Naunyn–Schmiedeberg's Arch Pharmacol, (2000) 361:319–326.
Rahimtoola, Shahbudin H., "The hibernating myocardium", American Heart Journal, (1989) vol. 117, No. 1, 211–221.
Savage et al., "Avidin–Biotin Chemistry: A Handbook", Pierce Chemical Company, pp. 1–13; 50–53 (1992).
Simons et al., "Clinical Trials in Coronary Angiogenesis: Issues, Problems, Consensus; An Expert Panel Summary", Circulation, Sep. 12, 2000, 102: 1–14.

(List continued on next page.)

Primary Examiner—Thurman K. Page
Assistant Examiner—Rachel M. Bennett
(74) Attorney, Agent, or Firm—Cameron, Kerrigan, Squire, Sanders & Dempsey L.L.P.

(57) ABSTRACT

Brief periods of occlusion of blood flow in an otherwise open target vessel adjacent to vessels supplying blood to an ischemic region are caused by periodic administration of a therapeutically effective amount of a vasoconstrictor. It is anticipated these brief periods of occlusion will induce the enlargement of collateral vessels, causing increased blood flow to the ischemic region.

15 Claims, 5 Drawing Sheets

OTHER PUBLICATIONS

Slepian, Marvin J., MD, "Polymeric Endoluminal Paving: A Family of Evolving Methods for Extending Endoluminal Therapeutics Beyond Stenting", Cardiology Clinics, vol. 12, No. 4, Nov. 1994, 715–737.

Soran et al., "Enhanced External Counterpulsation in the Management of Patients with Cardiovascular Disease", Clin. Cardiol., 22, 173–178 (1999).

Unger et al., "Acoustically ActiveLipospheres Containing Paclitaxel", Investigative Radiology, vol. 33, No. 12, 886–892 (1998).

Voelckel et al., "Effect of Small–Dose Dopamine on Mesenteric Blood Flow and Renal Function in a Pig Model of Cardiopulmonary Resuscitation with Vasopressin", Anesth Analg 1999; 89: 1430–6.

* cited by examiner

PERIODIC CONSTRICTION OF VESSELS TO TREAT ISCHEMIC TISSUE

BACKGROUND OF THE INVENTION

1. Field of the Invention

The invention provides methods and systems for the treatment of patients afflicted with coronary or peripheral artery disease. More particularly, the invention provides methods and systems for the treatment of ischemic tissue through a periodic, local administration of a vasoconstrictive drug to an open artery adjacent to regions of ischemic tissue.

2. Description of the Background

Ischemia is a condition which results from insufficient blood flow to an area of the body, usually due to an occlusion in a blood vessel. Ischemic heart disease results from insufficient coronary blood flow, which in turn is frequently caused by atherosclerosis. In certain persons who have a genetic predisposition to this condition, or in persons who eat excessive quantities of cholesterol and other fats, large quantities of cholesterol gradually become deposited beneath the intima (the innermost of three layers making up the blood vessel wall). Later, these areas of cholesterol deposit become invaded by fibrous tissue, and they also frequently become calcified. As a result, atherosclerotic plaque develops that protrudes into the vessels and either blocks or partially blocks blood flow. A very common site of development of atherosclerotic plaque is the first few centimeters of the coronary arteries, in which case the patient may suffer from myocardial ischemia.

FIG. 1 is an illustration of a mammalian heart 10. Major arteries for heart 10 include the right coronary artery ("RCA") 12, the left anterior descending artery ("LAD") 14, and the left circumflex ("LCX") 16. If an occlusion 18 were to develop at the top of LAD 14, then an ischemic region 20 (delineated by a hatch pattern) would develop within heart 10, because this region of the heart would not be receiving an adequate supply of oxygenated blood. In this case, LAD 14 may be termed an "occluded" vessel.

A compensatory mechanism is observed in some ischemic patients, wherein collateral vessels 22a, 22b, 22c, and 22d adjacent to ischemic region 20 enlarge so as to carry more blood from RCA 12 toward ischemic region 20. Of course, collateral vessels originating at LCX 16 could also (or alternatively) enlarge to carry more blood to ischemic region 20. This process is termed "arteriogenesis."

Occlusions and arteriogenesis are also seen in other areas of the body. For example, occlusions of the superficial femoral artery ("SFA"), which feeds blood to a person's leg, are common. In some patients, an enlargement of collateral vessels is observed, similar to the above-mentioned example of myocardial ischemia.

The precise mechanisms responsible for such arteriogenesis have not been definitively determined. A current theory is that arteriogenesis involves the concerted action of various growth factors, including vascular endothelial growth factor (VEGF), acidic and basic fibroblastic growth factors (aFGF and bFGF, respectively), platelet-derived endothelial cell growth factor (PD-ECGF), monocyte chemotractant factor (MCP1), and transforming growth factor $\beta_1$ (TGF-$\beta_1$). See, e.g., Simons et al., "Clinical Trials in Coronary Angiogenesis: Issues, Problems, Consensus" *Circulation*, 102:e73–e86, 2000; Chilian et al., "Microvascular Occlusions Promote Coronary Collateral Growth"*Am. J Physiol.*, 248 (4pt 2): H1103–11, 1995; Kersten et al., "DC Modulation of Coronary Collateral Angiogenesis: a Canine Model of Neo-vascularization Induced by Chronic Ischemia,"*J Card Surg*, 10:354–7, 1995; Sorman et al., "Enhanced External Counterpulsation in the Management of patients with Cardiovascular Disease,"*Clin. Cardiol.*, 22:173–8, 1999.

Since the precise mechanisms for arteriogenesis have not been definitively determined, currently no single method for stimulating arteriogenesis exists which offers proven, predictable, repeatable results. Methods being used in or considered for use in clinical trials include protein therapy and gene therapy.

Protein therapy involves the repeated administration of growth factor proteins to the patient. Protein therapy allows administration of precise amounts of growth factors with a well-defined half-life, pharmacokinetics, and safety record. Unfortunately, since the process of arteriogenesis is not fully understood, it is not known what growth factor protein, or combination of growth factor proteins, should be administered to the patient. Several methods may be used to administer the growth factor proteins, but each method has its drawbacks. Such methods include intravenous infusions, and for the specific case of myocardial ischemia, intracoronary infusions and intramyocardial delivery.

Intravenous infusions, while practical and low-cost, may result in undesirable side effects, such as nitric oxide-mediated hypotension, due to the high concentration of growth factor protein(s) required for systemic administration.

Intracoronary infusions are easily performed in a cardiac catheterization laboratory and are also applicable in most patients with coronary artery disease. However, the need for left heart catheterization limits this approach to a single session or, at most, infrequent repetitions. Moreover, intracoronary infusions may result in systemic exposure to the growth factor protein and may precipitate systemic hypotension. Finally, both intravenous and intracoronary infusions are associated with relatively low uptake in the target ischemic tissue. It has been observed that very small amounts of the growth factor (e.g., often less than 1%) remain in the ischemic myocardium one hour after intravenous or intracoronary administration.

Intramyocardial delivery is another method of delivering growth factor proteins, offering the advantages of targeting the desired areas of the heart, likely higher efficiency of delivery, and prolonged tissue retention. However, intramyocardial delivery is very invasive, requires highly specialized equipment, and requires a high skill level of the operator.

Theoretically, arteriogenesis could also be stimulated by the introduction of genes encoding growth factor proteins, rather than administration of the growth factor proteins themselves. An argument in favor of gene therapy is that it may facilitate sustained local production of growth factors by the patient. However, the use of gene therapy also has drawbacks. While conventional drugs work outside cell walls, the DNA encoding the growth factor(s) must penetrate not only the cell wall, but also the nucleus within the cell. The fraction of cells that actually take up and express the new DNA is quite low, typically a few percent, and at best 10–20%. Secondly, the DNA that actually enters the cell nuclei may be attacked by the patient's immune system. When the immune system is activated in this manner, the immune system may also harm healthy genes in the target cells and other nearby cells. Thus, gene therapy in its present form is associated with much more variability in the levels of the proteins produced and duration of expression than is protein therapy.

Thus, there is a need for a mechanism for stimulating arteriogenesis that does not suffer from the disadvantages described above.

SUMMARY

The present invention treats ischemia by causing brief periods of occlusion of blood flow in an otherwise open target vessel adjacent to the ischemic region. The periods of occlusion are caused by means of periodic administration of a therapeutically effective amount of a vasoconstrictor to the target vessel. It is anticipated that the periods of occlusion will re-route blood flow to collateral vessels, increase shear stress on these collateral vessels and cause them to release growth factor proteins. This, in turn, induces the enlargement of the collateral vessels, with the result of increased blood flow to the ischemic region. Thus, the invention contemplates stimulating the natural production of all growth factor proteins associated with arteriogenesis in a specific region of the body, rather than by the systemic or local administration of selected growth factor proteins, or local administration of DNA, as in the prior technology.

Exemplary modes of practicing the invention are discussed herein. In a first mode, delivery of a vasoconstrictor is achieved by means of an external or implanted pump system that stores and delivers the vasoconstrictor through an implanted catheter that extends between the pump and a selected portion of the target vessel. A preselected volume of the vasoconstrictor is periodically delivered from the pump to the target vessel. Each dose of the vasoconstrictor causes a brief period of occlusion of the target vessel, which induces shear stress in collateral vessels, and leads to the desired arteriogenesis. Advantageously, this mode of practicing the invention offers targeted delivery of a known quantity of the vasoconstrictor to arterioles at a specific region of the target vessel. Moreover, the vasoconstrictor can be administered multiple times to the patient over the course of weeks, with only two surgical procedures being performed if the embodiment including the implantable pump is used.

In a second mode of practicing the invention, a layer of polymer is deposited on the luminal surface of the target vessel. Microspheres that are adapted to attach to the layer of polymer are periodically injected into the patient's body. The microspheres contain a selected amount of the vasoconstrictor. Sufficient time is allowed for the microspheres to attach to the layer of polymer, where the microspheres subsequently release the vasoconstrictor. The vasoconstrictor causes a brief period of occlusion of the target vessel, which induces the above-mentioned shear stress in collateral vessels. As with the first mode, it is anticipated that the collateral vessels will enlarge over time due to the shear stress induced by occlusion of the target vessel, thereby developing increased blood flow to the ischemic region. Advantageously, the second mode of practicing the invention likewise offers targeted delivery of a known quantity of the vasoconstrictor to arterioles at a specific region of the target vessel. Moreover, the vasoconstrictor, being contained within a microsphere which is chemically bound to the wall of the target vessel, is not likely to be washed out from the vessel by diffusion and convection within the vessel into surrounding tissues.

Vasoconstrictors that may be used in accordance with the present invention, include, but are not limited to, epinephrine, norepinephrine, lysine vasopressin, 8-arginine vasopressin, angiotensin II, and methoxamine hydrochloride, and analogs of these compounds.

These and other aspects of the present invention may be better understood through the drawings and the following detailed description of the exemplary embodiments.

DETAILED DESCRIPTION OF THE EXEMPLARY EMIBODIMENTS

Figure 1:
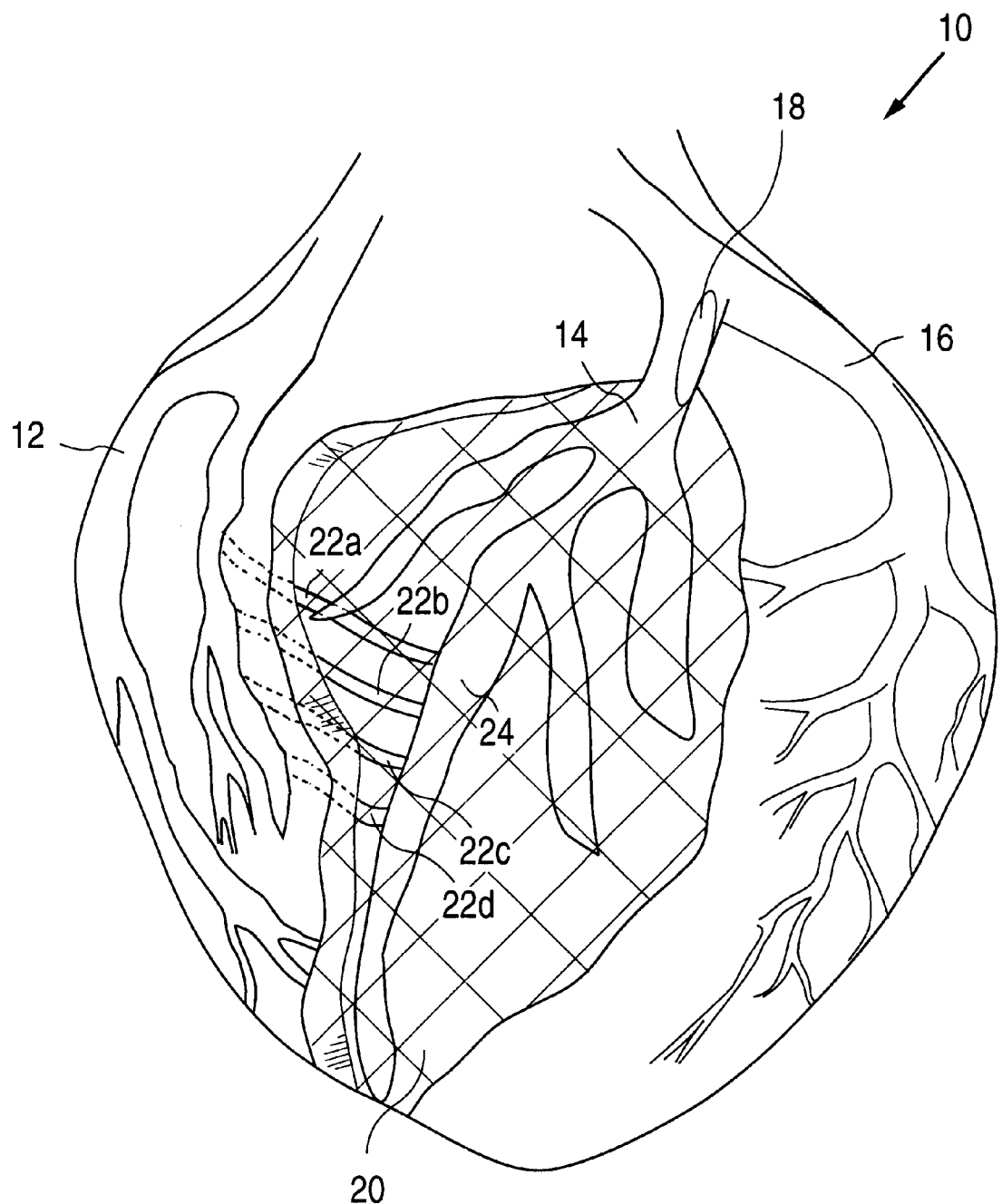
FIG. 1 is a schematic illustration of a mammalian heart.

Under a current theory of arteriogenesis, occlusion of a vessel creates an ischemic region and causes re-routing of blood flow to pre-existing smaller collateral arterioles located proximate to the occlusion. The increased flow velocity through these arterioles induces shear stress in the arterioles. Endothelial cells lining the arterioles sense this increase in shear stress, and the process of arteriogenesis is initiated. In some patients, under optimal conditions, the diameters of the arterioles increase to an extent that may nearly, or perhaps completely, compensate for the reduced blood flow through the main vessel. In accordance with the present invention, a vasoconstrictor drug (or drugs) is administered periodically in order to restrict blood flow in an open target vessel adjacent to an ischemic region. The temporary occlusion so produced re-routes the blood that normally would flow through the target vessel to pre-existing arterioles supplied from points upstream and downstream of the temporary occlusion. The increased shear stress experienced by cells in the arterioles is expected to release growth factors, degrade the cellular matrix, and cause proliferation of endothelial and smooth muscle cells. This causes lumen enlargement in the arterioles. The enlarged arterioles bring an increased volume of blood to the ischemic region. "Vasoconstrictor," as used herein, means a bioagent or combination of bioagents that cause a narrowing of a blood vessel. By way of example, and not limitation, the following bioagents are proposed for use as vasoconstrictors in conjunction with the present invention: epinephrine, norepinephrine, vasopressin, angiotensin II, lysine vasopressin, 8-arginine vasopressin, methoxamine hydrochloride and analogs of these compounds. The vasoconstrictor chosen ideally should have a half-life of not less than one minute, so that it is not eliminated by the patient's circulatory system before it exerts its vasoconstrictive effects. "Bioerodable," as used herein, means erodable by the action of the circulatory system in a mammal.

In practicing the invention, the target vessel selected should be located near an ischemic region of the patient. In particular, the target vessel should be a vessel wherein a periodic occlusion would be expected to cause increased amounts of blood to flow through collateral arterioles that also feed the ischemic region, albeit in much smaller volume. An angiogram or similar diagnostic methods may be necessary to determine an appropriate target vessel and site for the temporary occlusion.

Two modes of practicing the invention are described below. In the first mode, delivery of a vasoconstrictor is achieved by means of an external or implantable pump system that stores and delivers the vasoconstrictor, and a catheter that extends between the pump and the target vessel and delivers the vasoconstrictor to the target vessel. In the second mode, delivery of a vasoconstrictor is achieved by first depositing a layer of polymer on the luminal surface of a target vessel, and then injecting microspheres containing a vasoconstrictor into the patient. The microspheres are adapted to attach to the layer of polymer and release the vasoconstrictor. Since the first mode of practicing the invention is somewhat less complicated, it is discussed first, followed by the second mode of practicing the invention.

1. Use of External or Implantable Pump and Catheter to Deliver the Vasoconstrictor This mode of practicing the invention is feasible at any site of the body, but perhaps is most suitable for use in peripheral regions of a patient, such as the superficial femoral artery (SFA), rather than in the coronary region.

Figure 2A:
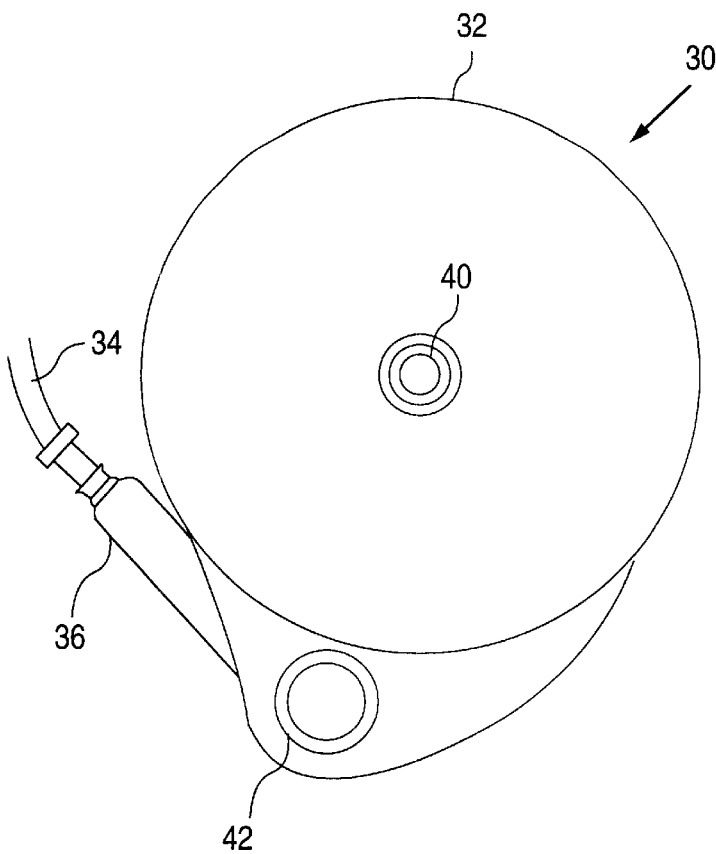
FIG. 2A is a top view of an implantable pump for use in delivering a vasoconstrictor to a target vessel in accordance with an embodiment of the present invention.
Figure 2B:
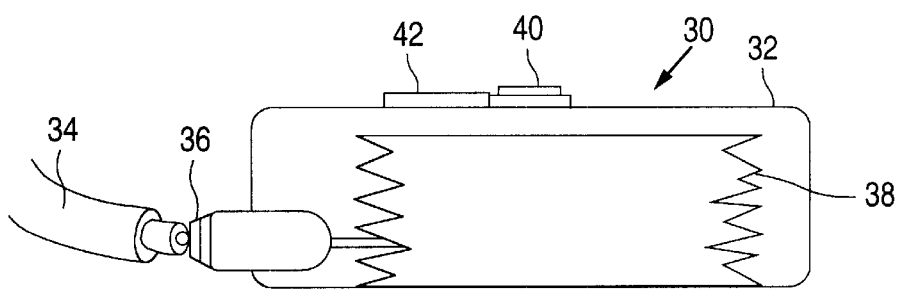
FIG. 2B is a side view of the implantable pump of FIG. 2A.

FIG. 2A illustrates an exemplary pump system 30, along the lines of the Synchromed® Infusion System that is commercially available from Medtronic, Inc., of Minneapolis, Minn. Pump system 30 includes a round implantable pump 32 and an implantable hollow catheter 34 connected to an output port 36 of pump 32. Pump 32 includes a titanium body that is about 2.5 cm thick and 8.5 cm in diameter. Pump 32 may be surgically implanted in, for example, the peritoneal cavity of the patient. Referring now to FIG. 2B, pump 32, which provides an "xray" view of pump system 30 from the side, has a collapsible reservoir 38 for storing the vasoconstrictor. Reservoir 38 is supplied through a reservoir fill port 40. Reservoir 38 may be filled or refilled with vasoconstrictor by passing a syringe through the peritoneal cavity of the patient and into reservoir fill port 40. Pump 32 further includes a side catheter access port 42 that allows the physician to inject the vasoconstrictor, other medication or sterile solutions directly into catheter 34, bypassing pump 32.

A pumping mechanism (not shown) within pump 32 propels a solution of the vasoconstrictor from reservoir 38 through output port 36 to catheter 34. Pump 32 also includes a control system (not shown), typically including a microprocessor and memory, for operating the pumping mechanism in accordance with a treatment regime stored in the memory. Pump 32 also includes a battery for power and a radio-frequency (RF) receiver (not shown). The RF receiver allows pump 32 to receive new instructions from an external computer and RF transmitter for storage in the memory should the treating physician decide to change the treatment regime. For example, the physician may adjust parameters such as flow rate, infusion period, ramp time, and bolus volume. Pump 32 may also include a radio transmitter for transmitting operational data to the external computer for monitoring purposes.

Figure 3:
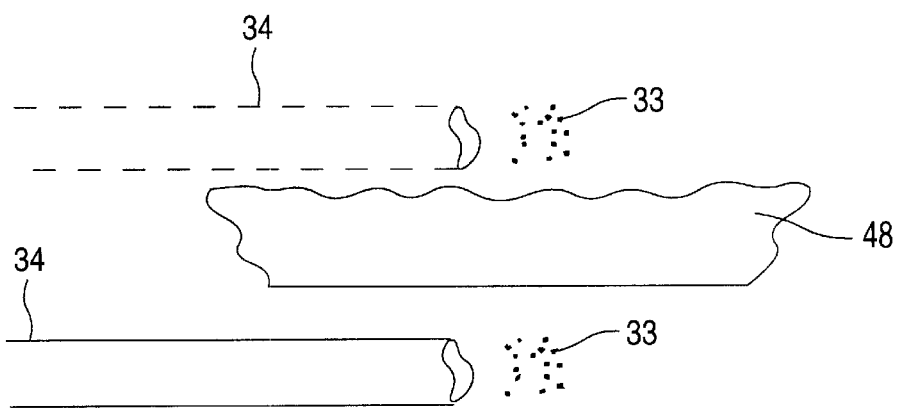
FIG. 3 is a cross-sectional view of a catheter implanted at a selected region of the target vessel.

As mentioned above, pump system 30 is implanted in the patient's body. FIG. 3 shows the open end of catheter 34 positioned adjacent to the desired point of occlusion of a target vessel 48. For example, if the SFA is occluded, then the deep femoral artery may be target vessel 48. Catheter 34 may be positioned either intraluminally, within target vessel 48 (as illustrated by catheter 34 having a solid line), or periadventitially (as illustrated by catheter 34 having a broken line). A preselected volume of vasoconstrictor 33 is delivered from pump 32 through catheter 34 to target vessel 48. Delivery of the preselected volume of vasoconstrictor 33 is repeated at a preselected periodic interval. For example, the pump may be programmed to deliver a dose of approximately 0.07 micrograms of norepinephrine in a two minute period eight times a day for a period of twenty-two days. After the prescribed therapy regimen is completed, implantable pump 32 and catheter 34 are removed from the patient.

In another embodiment, an external pump is used in conjunction with an implanted catheter that is accessible through the patient's skin.

Figure 4A:
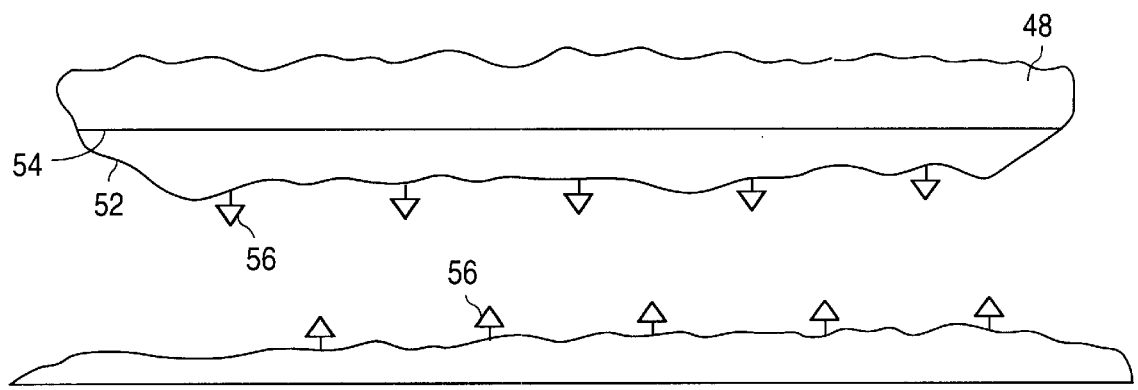
FIGS. 4A, 4B, and 4C are cross-sectional views of phases of a method for treating ischemia in accordance with an embodiment of the present invention.
Figure 4B:
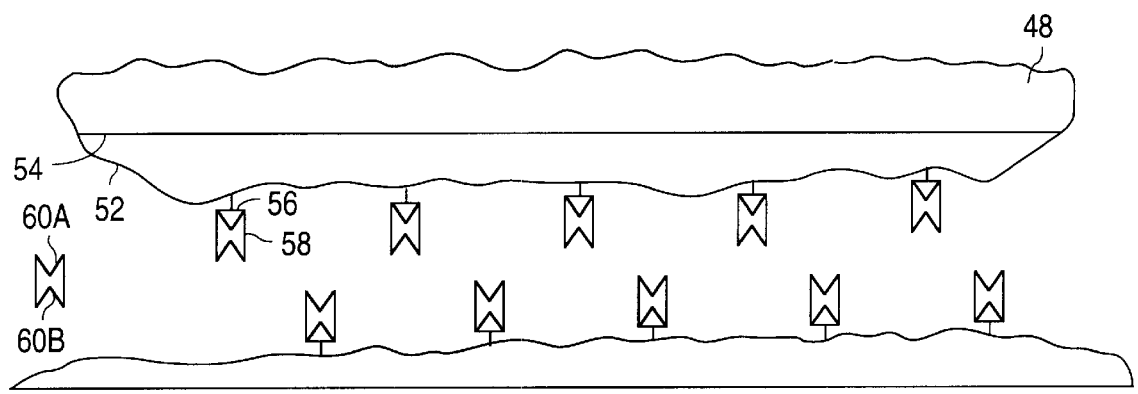
Figure 4C:
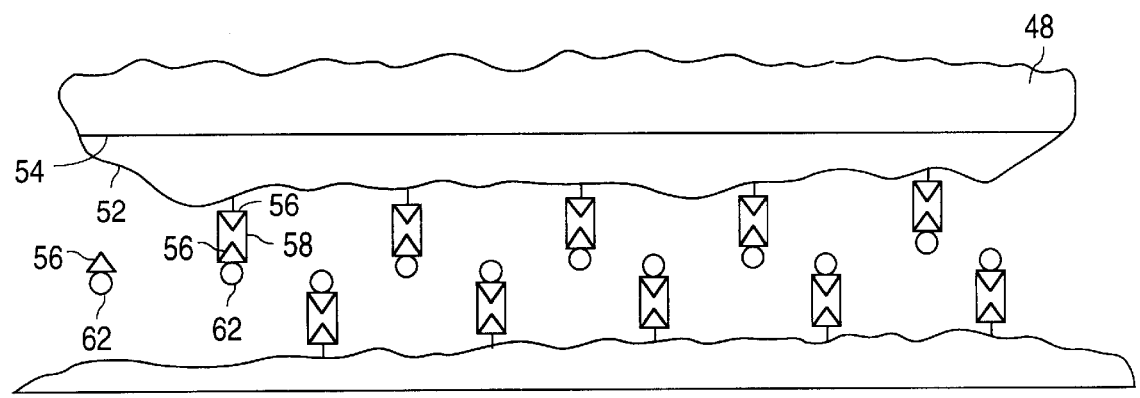

2. Use of Polymer Target and Affinity Pair Members to Deliver the Vasoconstrictor FIGS. 4A–4C illustrate phases of an exemplary method for periodically administering a vasoconstrictor to an open target vessel, in accordance with another embodiment of the invention. Referring to FIG. 4A, the method includes selecting an open target vessel 48, and depositing a layer of a polymer 52 on a luminal surface 54 of target vessel 48. The layer of polymer 52 includes first members 56 (e.g., biotin) of an affinity pair to which another affinity pair member will subsequently be attached (hence the layer of polymer 52 is considered a target). The layer of polymer 52 may be deposited on luminal surface 54 by several methods, as is discussed below.

As illustrated in FIG. 4B, receptor molecules 58 are provided to target vessel 48. Receptor molecules 58 include second members (e.g., avidin) of the affinity pair. The second members of receptor molecules 58 bind to first members 56 of the layer of polymer 52 at a binding site 60A. Receptor molecules 58 may have at least two binding sites 60A and 60B in one embodiment of the invention. Receptor molecules 58 are thereby bound to the first members 56 of the affinity pair of polymer 52 at first binding site 60A.

Referring now to FIG. 4C, microspheres 62 are injected into the patient's bloodstream. In one embodiment, microspheres 62 (erodable in the bloodstream) contain a vasoconstrictor. The surface of microspheres 62 also includes first members 56 of the affinity pair, which can bind to the second members of receptor molecules 58 at second binding site 60B. For example, microspheres 62 may contain epinephrine and have biotin attached to their surfaces as first members 56.

Still referring to FIG. 4C, time is allowed for microspheres 62 to collect at the site of the layer of polymer 52 due to the binding of first and second members 56, 58 of the affinity pair. If avidin and biotin are used as the members of the affinity pair, for example, virtually all (greater than 95%) of the avidin or biotin injected into the bloodstream will collect at target vessel 48 within two minutes. Alternately, the affinity pair may be, for example, a highly specific antigen-antibody pair, which does not possess specific binding capacity to vascular components (e.g., blood plasma, blood cells, and vessel wall).

Erodable microspheres 62 collect at target vessel 48, releasing the vasoconstrictor and thereby causing a temporary occlusion of target vessel 48. The time required for erosion of microspheres 62 can be manipulated by the way microspheres 62 are made, as will be explained below.

The steps of the method are then repeated in accordance with a prescribed therapy regimen. For example, doses of approximately 0.07 micrograms of norepinephrine may be delivered to target vessel 48 in microspheres 62 eight times per day for a period of twenty-two consecutive days by injecting albumin microspheres 62 containing norepinephrine. Such a dosage may be delivered, for example, by injecting 1 cc of a solution containing 0.01% (by weight) microspheres 62, where microspheres 62 are prepared in accordance with the method described below in Example 3, using norepinephrine as the drug. The exact loading of microspheres 62 and the number of microspheres 62 to be injected will reflect the collection efficiency of the layer of polymer 52 and the pharmacokinetics of the vasoconstrictor. The collection efficiency of the layer of polymer 52, in turn, is affected by several factors, including the polymer selected, the number of first members 56 per unit area of the layer of polymer 52, and the elapsed time between injection of receptor molecules 58 and injection of microspheres 62.

After the prescribed therapy regimen is completed, the layer of polymer 52 on luminal surface 54 of target vessel 48 harmlessly dissolves.

Advantageously, this method provides a very localized delivery of the vasoconstrictor, due to the attraction of the first and second members of the affinity pair for each other. Since the vasoconstrictor is chemically bound to the wall of target vessel 48 by the action of first and second members 56 and 58 of the affinity pair, the vasoconstrictor is not likely to be washed out from target vessel 48 by diffusion and convection within target vessel 48 into surrounding tissues. Accordingly, lower dosages of vasoconstrictor can be provided, while still achieving the desired effects.

Further details of the above-described method, including information concerning attachment of first members 56 to the polymer layer, application of the polymer layer to luminal surface 54 of target vessel 48, and microspheres 62 and their preparation, are provided below.

According to another embodiment of the present invention, receptor molecules are not used. Rather, polymer 52 and microspheres 62 include the first and second members 56, 58 of the affinity pair, respectively. For example, biotin is included in the layer of polymer 52, and avidin is included on the surfaces of microspheres 62. Microspheres 62 collect at the site of the layer of polymer 52 due to the binding of the first and second members 56, 58 of the affinity pair. Details regarding the attachment of avidin molecules to microspheres 62 are provided in Example 6 below.

2A. Affinity Pairs for the Polymer Layer

First members 56 of a highly specific affinity pair may be attached to the layer of polymer 52 by methods well known to one of ordinary skill in the art. As mentioned above, biotin ($C_{10}H_{16}N_2O_3S$), and avidin, may be used as the members of the affinity pair. Avidin is a polypeptide composed of at least 128 amino acid residues. Typically, however, a single avidin polypeptide chain is a subunit associated with three essentially identical polypeptide chains, forming a tetramer. An avidin tetramer will bind four biotin molecules in solution in a noncovalent interaction that has a binding constant of about $10^{15} M^{-1}$, has a half-life in vivo of about 89 days, and is essentially undisturbed by organic solvents.

The avidin and/or biotin molecules may be further modified chemically to change the binding constant of an avidin tetramer. This may be desirable, for example, to ensure that all avidin molecules are detached from the avidin tetramer between successive administrations of microspheres 62 containing the vasoconstrictor.

Avidin and biotin can be used interchangeably as first member 56 and second member 58 of the affinity pair. However, avidin is a large molecule, and is multivalent, being able to bind to four biotin molecules simultaneously. Moreover, avidin is less stable in vivo than biotin is. Consequently, we believe better results may be obtained in this embodiment if biotin is attached to the layer of polymer 52, rather than avidin, and if avidin is attached to microspheres 62, rather than biotin (e.g., biotin is first member 56 and avidin is second member 58 in the embodiment illustrated in FIGS. 4A–4C).

Biotin can be bound to polymer 52 using a photoactivatable form of biotin, in conjunction with photoactivation. Photoactivatable biotin has a low specificity for functional groups, and thus may be used with a wide variety of polymers. An exemplary procedure for binding biotin to a polymer is described in Example 1 below.

Other substances may be used as members of the affinity pair. For example, streptavidin and ExtrAvidin® (a modified avidin reagent available from Sigma-Aldrich Corporation, St. Louis, Mo.) may be used instead of avidin. Streptavidin is isolated from a culture broth of Streptomyces avidinii. Although avidin and streptavidin have similar affinities for biotin, they are very different in other respects. Avidin is very soluble in aqueous solutions, while streptavidin is less soluble in water and can be crystallized from water or 50% isopropanol. Likewise, iminobiotin may be used as a substitute for biotin, although avidin and strepatvidin molecules will not bind as tightly to iminobiotin as they do to biotin.

2B. Application of the Polymer Layer to the Luminal Surface of the Target Vessel Referring again to FIG. 4A, the layer of polymer 52 may be deposited on luminal surface 54 of target vessel 48 using a stent. The stent can be self-expanding or expanded by a dilatation balloon.

The stent can be formed from a polymeric material, either permanent or biodegradable. Alternatively, a metallic stent having a polymer coating may be used. However, since the stent serves the temporary function of providing a substrate for attachment of a vasoconstrictor to luminal surface 54 of target vessel 48, a biodegradable stent is most useful.

Since the stents used for this application are not intended to provide mechanical support for a vessel for extended periods of time, which is the typical purpose of a stent, but rather are used as a temporary substrate, a much larger range of physical properties and degradation rates can be used than what would be suitable for a stent that is used in combination with angioplasty. Suitable biodegradable polymers for preparing such useful stents include, but are not limited to: polylactic acid (PLA), poly-glycolic acid (PGA), polyphosphazenes, poly-hydroxybutyric acid, poly-caprolactone and poly-anhydrides. Copolymers of PLA and PGA can be made to erode in a time frame of six to ten weeks. For example, a copolymer having a 50/50 mixture (by weight) of PLA and PGA may be used to yield a useful life of six weeks. Copolymers with more PLA than PGA will result in slower erosion rates, and thus a longer useful life.

A method for shortening the erosion time of PLA and PGA and their copolymers is to increase their hydrophilicity by, for example, incorporating segments of polyethylene glycol (PEG) in them. Incorporation of PEG will reduce the life span of the original polymer by up to 50% (by making the original polymer more hydrophilic, causing it to absorb water and degrade more quickly). Thus, in the example above, incorporation of 50% by weight PEG into the 50/50 mixture of PLA and PGA will reduce the useful life of the polymer to three weeks. For very short residence times, e.g., three weeks, a copolymer of 50% PLA/PGA and 50% PEG would be useful.

The stents can be made by injection molding or by an extrusion and braiding process. In general, stents with a higher crystallinity (e.g., pure PLA or PGA) will have higher elasticity, and will be more suitable as self-expanding stents. Stents with low crystallinity, and lower molecular weights will be more suitable for stents expanded by a dilatation balloon.

Methods for producing stents with a biodegradable polymer coating are well-known in the art, as exemplified by U.S. Pat. No. 5,464,650 issued to Berg et al., U.S. Pat. No. 5,605,696 issued to Eury et al., and U.S. Pat. No. 5,700,286 issued to Tartaglia et al. The disclosures of these three patents are incorporated by reference herein.

The polymer used to make the stent may be treated in a manner that incorporates first members 56 of the affinity pairs on the luminal surface of polymer 52, as described in Example 1 below.

According to another embodiment within this mode of practicing the invention, the layer of polymer 52 deposited on luminal surface 54 of target vessel 48 is a polymeric endoluminal gel. Use of a polymeric endoluminal gel rather than a stent may be appropriate when the total desired time for delivery of the vasoconstrictor is short (e.g., 7 to 14 days) or when the target vessel geometry is more tortuous, making deployment of a stent in that area more difficult.

The process of locally forming, molding or adapting biocompatible polymers to underlying tissue topography, while at the same time generating a smooth endoluminal surface, has been termed "endoluminal paving." Polymeric endoluminal paving, in its generic form, is a process wherein biocompatible polymers may be applied via catheter to the endoluminal surface of an organ or organ component (e.g., RCA 12 of FIG. 1) and customcontoured in situ to yield a layer of polymer 52 in intimate contact with the underlying tissue surface.

Hydrogels may be used as the polymeric material for paving the endoluminal surface of a vessel. Hydrogels are polymeric materials that are significantly swollen, but not dissolved, by water. The physical properties of hydrogels are largely influenced by the ratio of solids to water and the degree of cross-linking, and can range from loose watery materials to stiff, near-solid materials.

Figure 6:
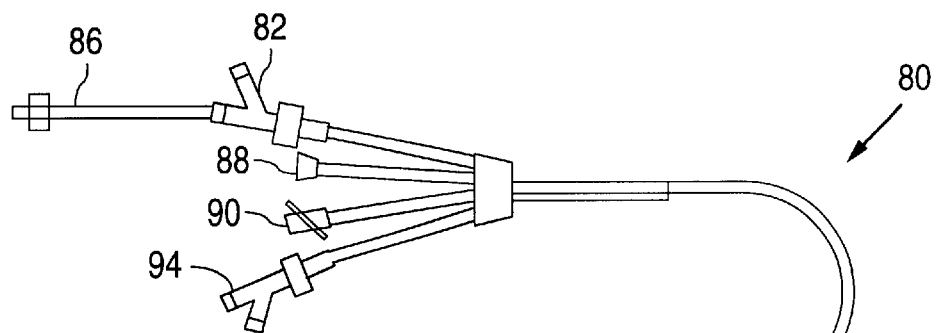
FIG. 6 is a side view of an in situ photopolymerization gel paving catheter system, which is used in one embodiment for depositing a layer of bioerodable, polymeric material on the luminal surface of a selected blood vessel.
Figure 6:
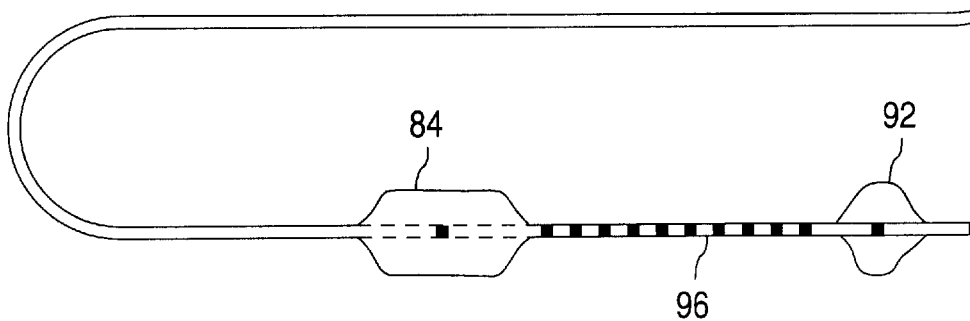

Hydrogels that polymerize when subjected to light of a certain wavelength may be formed percutaneously on vascular endoluminal surfaces using a catheter. An example of a representative catheter 80 for in-situ polymeric endoluminal paving using a photo-polymerization technique is illustrated in FIG. 6. Catheter 80 includes a port 82 for inflation/deflation of a proximal balloon 84 and delivery of light through a fiberoptic light source 86, a flush lumen 88, a port 90 for inflation/deflation of a distal balloon 92, a guidewire lumen 94, and a flushing sheath 96.

If the hydrogel precursor contains amines, then first members 56 (in an example case, biotin) of the affinity pair may be attached by biotinylation. The hydrogel precursor may be biotinylated according to the albumin biotinylation protocol described in Example 2 below, except that the hydrogel precursor is substituted for albumin. If the hydrogel precursor does not contain amines, then it may be biotinylated via the protocol for photoactivatably biotinylating polymers described in Example 1 below.

Hydrogel precursors containing amines are more easily biotinylated than hydrogel precursors without amines. Moreover, primary amines are more easily biotinylated than secondary and tertiary amines. Accordingly, hydrogel precursors containing large numbers of primary amino groups are desirable. For example, branched polyethylenimine (available from Polysciences, Inc. of Warrington, Pa.) is a highly branched polyamine with high charge density, containing primary, secondary, and tertiary amine groups in approximately a 1:1:2 ratio.

Figure 7A:
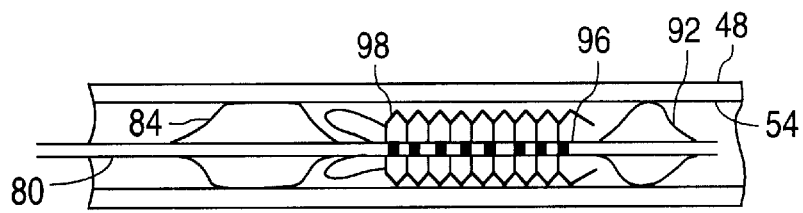
FIGS. 7A–7C illustrate the process of in situ photopolymerization of hydrogel paving layers using the catheter system illustrated in FIG. 6.
Figure 7B:
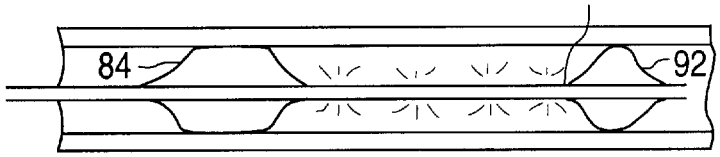

As illustrated in FIG. 7A, catheter 80 is positioned within the desired portion of open target vessel 48. Proximal balloon 84 is inflated by a syringe which connects to port 82, which typically delivers saline to proximal balloon 84. Photoinitiator dye is delivered through flush lumen 88 to flushing sheath 96. The photoinitiator dye displaces blood downstream of proximal balloon 84, and stains luminal surface 54 of target vessel 48. Distal balloon 92 is inflated by a syringe connected to port 90, which provides saline to distal balloon 92. A flowable macromeric precursor 98 of the biotinylated hydrogel is then delivered through flush lumen 88 and flushing sheath 96 to the desired region of hydrogel formation, as illustrated in FIG. 7A. The region is briefly illuminated via light transmitted through fiberoptic light source 86, which is guided toward the distal end of catheter 80, as illustrated in FIG. 7B. The light (indicated by radiating beam lines in FIG. 7B) causes polymerization of the biotinylated hydrogel at the stained tissue-macromer interface. Polymerization of the biotinylated hydrogel leads to radial expansion of the bitoinylated hydrogel in a direction inward from the tissue surface toward the center line of the lumen. Distal balloon 92 and proximal balloon 84 are then deflated, and catheter 80 is removed.

Figure 7C:
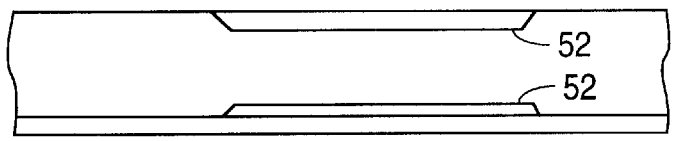

As a result of the above-described endoluminal paving process, a smooth layer of biotinylated hydrogel (i.e., polymer layer 52) is deposited on the endoluminal surface 54 of target vessel 48, as illustrated in FIG. 7C. Catheter-based formation of hydrogels using the system just described typically can be performed over a 30–40 second period in coronary and peripheral arteries.

After the smooth layer of biotinylated hydrogel is deposited, (thereby forming polymer layer 52 of FIGS. 4A and 7C) receptor molecules 58 (e.g., second members comprising avidin) may be injected systemically. Biotinylated microspheres 62 may then be injected systemically, as described earlier. Once microspheres 62 are bound to the polymer layer 52, the vasoconstrictor is released by, for example, bioerosion or rupture due to an external stimulus (e.g., ultrasound).

Further examples of polymeric endoluminal paving techniques are provided in U.S. Pat. No. 5,749,222 issued to Slepian, et al., which is incorporated herein by reference.

2C. Selection and Preparation of Microspheres

In one embodiment of the invention, microspheres 62 (containing the vasoconstrictor) are composed of albumin. The albumin may be derived from, for example, a cow (bovine serum albumin ("BSA")), a human, a sheep, a rat, or a goat. Advantageously, albumin is a biological protein, and as such, is biocompatible. The time required to erode albumin microspheres 62, and thus to release the vasoconstrictor from microspheres 62, can be governed by the degree of cross-linking. Biotinylated albumin microspheres 62 may be produced by several methods, some of which are described under Examples 3 through 6 below.

In accordance with another embodiment of the invention, microspheres 62 are composed of a polymeric material, such as PLA or PGA. Biotinylated polymeric microspheres 62 may be produced by several methods, one of which is provided in Example 8 below.

In another embodiment, microspheres 62 are composed of a lipid material, such as phosphatidylserine, in which case they are also known as liposomes. Liposomes to which biotin molecules are attached (and are therefore said to be "biotinylated") may be produced by several methods, one of which is provided in Example 9 below.

Regardless of the material from which microspheres 62 are made, the vast majority of microspheres 62 (i.e., 90% or more) should have an outside diameter of four microns or less. This diameter corresponds to the diameter of a red blood cell. Microspheres 62 larger in diameter than four microns may become lodged in the capillary bed, obstructing flow through the vasculature in which the capillary bed is situated. The examples listed below yield a majority of microspheres 62 having an outside diameter of four microns or less. Any larger microspheres may be removed from the set produced by methods known to those of ordinary skill in the art, such as filtering.

2D. Release of Vasoconstrictor from Microspheres

As mentioned above, the vasoconstrictors may be released by simple erosion of microspheres 62 after attachment to the polymer layer 52. In accordance with an alternative embodiment within the present invention, microspheres 62 that are susceptible to rupture by the application of an external stimulus may be used. An example of such an external stimulus is ultrasound energy provided by a transmitter that is external to the patient's body.

Figure 5:
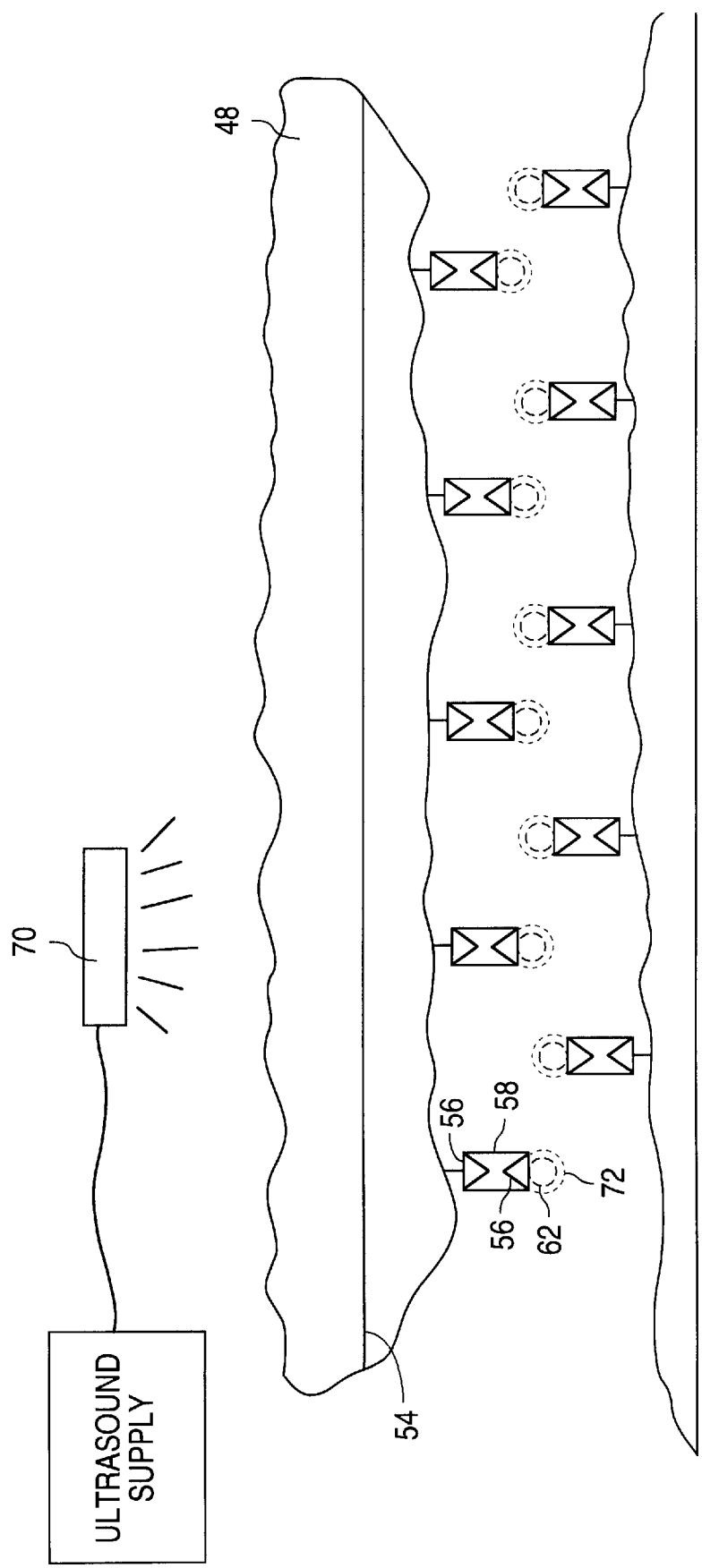
FIG. 5 illustrates release of a vasoconstrictor from microspheres upon application of an ultrasound signal provided by a transmitter in accordance with one embodiment of the present invention.

Referring now to FIG. 5, an ultrasound transmitter 70 is positioned so that an effective amount of ultrasound energy may be transmitted to microspheres 62 that are bonded to the polymer layer 52 by first member 56 of the affinity pair and receptor molecules 58 (which include second members of the affinity pair). The ultrasound energy provided by transmitter 70 causes microspheres 62 to rupture, thereby releasing the vasoconstrictor within microspheres 62.

Typically, microspheres 62 used for the embodiment employing ultrasound would be bioerodable, like microspheres 62 described above, but would erode at a slower rate due to changes in the preparation method. For example, microspheres 62 may be made to erode more slowly by increasing the degree of cross-linking between the polymer molecules that make up microspheres 62. A higher degree of cross-linking may be attained by increasing the heat treatment time or increasing the concentration of cross-linking reagent. For instance, using the protocol described below in Example 3, the suspension mixture may be stirred at a temperature of 90° C. for thirty minutes, instead of fifteen minutes. Alternately, using the protocol described below in Example 4, the particle solution may be treated with a 3% aqueous glutaraldehyde solution at a 10:1 ratio, instead of 1%, or the ratio may be decreased to 5:1. Advantageously, more erosion-resistant microspheres 62 could be directed by the circulatory system through target vessel 48 multiple times before eroding, providing multiple opportunities for microspheres 62 to attach to polymer layer 52 in target vessel 48. Consequently, the efficiency of delivery of the vasoconstrictor (contained in microspheres 62) to target vessel 48 will be increased.

Microspheres 62 may be forced to rupture by directing ultrasound energy from, for example, a 100 kHz therapeutic ultrasound transmitter, operated in a pulsed-wave mode at a 7% duty cycle for one minute through the patient's chest or back toward polymer 52 in target vessel 48. Advantageously, operating the transducer in a pulsed-wave mode results in a higher maximum temporal intensity, while the time-averaged intensity is low. For example, if ten operating cycles are provided per minute, with each cycle lasting six seconds, then the transducer will be activated for 7% of each cycle (0.42 seconds) and inactive for the remaining portion of the cycle (6.58 seconds). Since microspheres 62 containing the vasoconstrictor primarily collect at polymer 52 (due to the attraction of the first 56 and second 58 members of the affinity pair for one another in one embodiment), a broadly focused ultrasound beam (e.g., focused on the entire heart, rather than selected portions of it) will nonetheless result in targeted delivery of the vasoconstrictor. The rate at which microspheres 62 will rupture is typically dependent upon the power delivered by the ultrasound signal.

Other methods for making microspheres 62 rupture using ultrasound are known in the art. For example, U.S. Pat. No. 5,770,222 issued to Unger, et al. describes such therapeutic drug delivery systems. The disclosure of the Unger, et al. patent is incorporated by reference herein.

Gas-filled liposomes also may be used, instead of using microspheres 62, in an ultrasound embodiment as a vehicle for the vasoconstrictor. Advantageously, gas-filled liposomes are extremely sensitive to ultrasound signals, and the location of the liposomes within the circulatory system after injection may be easily tracked by using various imaging techniques.

In embodiments where ultrasound energy is used to trigger the release of the vasoconstrictor, the timing of delivery of the vasoconstrictor to target vessel 48 is precisely known, because release of the vasoconstrictor is coincident with the application of the ultrasound signal, rather than being dependent upon the rate of erosion of microspheres 62 (which can be accurately estimated, but not controlled with the same precision).

In accordance with another ultrasound embodiment of the present invention, target vessel 48 is selected. Microspheres 62 containing a vasoconstrictor are injected into the patient's bloodstream. In this embodiment, however, a layer of polymer 52 is not applied in target vessel 48 in order to fix the site of the temporary occlusion. Rather, the site of the occlusion is fixed by careful aiming of a finely focused ultrasound beam. In particular, microspheres 62 are injected systemically, and then a very finely focused ultrasound signal is applied to target vessel 48 for a predetermined period using transmitter 70. Microspheres 62 rupture and release the vasoconstrictor when they flow under the ultrasound beam. Since target vessel 48 will be moving, its location should be tracked and vessel location data should be sent back to the transmitter to focus the ultrasound signal, in order to prevent microspheres 62 present in vessels other than target vessel 48 from being exposed to ultrasound. Microspheres 62 that are not ruptured by the ultrasound signal are cleared by the circulatory system.

3. Appropriate Patient Population and Overview of Therapy Regimen

Good candidates for the methods described herein are patients with at least one open major blood conduit adjacent to the occluded vessel and/or ischemic region. For example, if the patient's RCA and LCX are occluded, and the LAD is open, then the patient may be suitable for this treatment. Patients suffering from peripheral artery disease (e.g., critical limb ischemia or claudication) likewise should have at least one open vessel to deliver the therapy. For example, if the patient's SFA is occluded, but the deep femoral artery is open, then the patient may be suitable for this treatment.

The period of time required for inducing arteriogenesis is anticipated to be substantial, e.g., several weeks.

Accordingly, the treatment proposed herein may have limited, if any, applicability to patients having acute conditions. For example, patients suffering from an acute myocardial infarction, or patients with peripheral artery disease who are at risk for immediate limb loss, may be less suitable for such a treatment regime.

Administration of the vasoconstrictor via the various embodiments disclosed herein should be intermittent and applied via multiple treatments. The number of temporary occlusions to be induced by periodic delivery of the vasoconstrictors may be between five and ten temporary occlusions per day over a period of two to eight weeks. Clinically, the therapy regimen ultimately prescribed would be determined by the health of the patient (e.g., degree of angina for a patient with coronary artery disease), and the observed effectiveness of the therapy.

The dosage or concentration of vasoconstrictor required to treat the ischemia should be less than that at which the vasoconstrictor produces toxic effects, and greater than the level at which non-therapeutic results are obtained. For example, the dosage of vasoconstrictor may be calculated such that the vasoconstrictive effect (i.e.,. narrowing of the lumen of the target vessel) lasts at least 30 seconds, but less than two minutes. Occlusion events longer than two minutes may lead to irreversible damage of the myocardial cells.

We estimate that, according to one treatment regimen, approximately 12 micrograms of norepinephrine, or 39 micrograms of vasopressin, should be provided over a 22-day period to treat an ischemic region. This estimate assumes a blood flow rate through target vessel 48 of the patient is about 0.01 mL/minute, and a target vessel occlusion time of two minutes. This estimate also assumes occlusions are provided eight times a day for 22 days, and that an effective vasoconstrictor concentration of $1\times10^8$ M in the plasma would cause the temporary occlusions.

Therapeutically effective dosages of the vasoconstrictor can be determined empirically, for example, by infusing target vessels in vivo with the vasoconstrictor and using fluoroscopic methods to determine the amount of vasoconstrictor required to produce a desired vasoconstrictive effect. The event of vessel occlusion in an animal model may be determined using, for example, angiography or a flow wire. Standard pharmacokinetic test procedures to determine dosages are understood by one of ordinary skill in the art.

EXAMPLE 1

Preparation of Biotinylated Polymer Using Photoactivable Biotin

Prepare a 4 mg/mL sample of a polymer in aqueous solution or in alcohol in an Eppendorf tube. Add photoactivatable biotin to the sample solution at a molar biotin:polymer ratio of 5:1. Vortex the mixture and place on ice. Irradiate the open Eppendorf tube at a distance of 20 cm in a vertical position for 20 minutes. The optimum wavelength for photoactivation is 350 nm. A suitable lamp for providing this wavelength of light is a high intensity mercury vapor lamp, 250 W. The biotinylated polymer is then ready for use. Advantageously, photoactivatable biotin reacts with a variety of polymers, including PLA and PGA.

EXAMPLE 2

Albumin Biotinylation Protocol

According to this protocol, a stock solution of a water-insoluble NHS ester of biotin ("stock biotinylation reagent") at a concentration of 0.088 mmol/ml is prepared. This may be achieved by dissolving 3 mg NHS-biotin in 100 $\mu$L of DMSO or 4 mg NHS-LC-biotin II in 100 $\mu$L of DMSO. In the first step of the protocol, 10 mg of albumin (e.g., BSA) is dissolved in 1 mL of 0.1 M sodium diphosphate, pH 7.2. Then, 25 $\mu$L of stock biotinylation reagent is added, and stirred gently at room temperature for ten minutes. An additional 25 $\mu$L of stock biotinylation reagent is added, and stirred gently at room temperature for an additional twenty minutes. Unreacted and hydrolyzed stock biotinylation reagent is removed by centrifuging the product at 1000×g for 15–30 minutes using a microconcentrator. After centrifuging, the sample is brought up to its original volume with sodium phosphate buffer. The process of centrifugation, followed by addition of sodium phosphate buffer, is repeated two more times. The concentration of albumin may then be determined by spectrophotometry, with absorbance measured at a wavelength of 280 nm. The biotinylated albumin is stored at 4° C. until ready for use, or may be frozen.

EXAMPLE 3

Preparation of Biotinylated Albumin Microspheres by Thermal Crosslinking

Attach biotin to albumin according to the albumin biotinylation protocol given in Example 2. Add the vasoconstrictor to a solution of biotinylated albumin in water that is 20% by weight albumin, such that a drug:albumin weight ratio of 1:2 is obtained. The resulting drug:albumin solution is then ultrasonicated in cottonseed oil for 30 minutes, with a weight ratio of cottonseed oil: drug:albumin solution of 80:1. The resulting suspension mixture is then added to an equal volume of cottonseed oil preheated to 90° C. The mixture is then stirred at this temperature for 15 minutes. The resulting solution is then cooled to room temperature and diluted with 4:1 diethyl ether (majority diethyl ether). Albumin particles (microspheres 62) are obtained by centrifugation and repeated dilutions. The microspheres may be freeze-dried for storage.

EXAMPLE 4

Preparation of Biotinylated Albumin Microspheres by Chemical Crosslinking

Attach biotin to albumin according to the albumin biotinylation protocol given in Example 2. Add the vasoconstrictor to a solution of biotinylated albumin in water that is 20% by weight albumin, such that a drug:albumin weight ratio of 1:2 is obtained. The resulting drug:albumin solution is then ultrasonicated in cottonseed oil for 30 minutes, with a weight ratio of cottonseed oil: drug:albumin solution of 80:1. The resulting solution is then cooled to room temperature and diluted 4:1 with diethyl ether (majority diethyl ether). Albumin particles (i.e., microspheres 62) are obtained by centrifugation and repeated dilutions. The particle solution is then treated with a 1% aqueous glutaraldehyde solution at a 10:1 ratio (majority particulate solution). The microspheres may be freeze-dried for storage.

EXAMPLE 5

Preparation of Biotinylated Albumin Microspheres by Spray Drying

Attach biotin to albumin according to the albumin biotinylation protocol given in Example 2. Dissolve drug and albumin in water (2:1 ratio of albumin:drug by weight) to form a 1% by weight aqueous solution. Spray dry using an appropriate apparatus. (for example, Model 190 spray dryer, BUCHI Laboratoriums-Technik AG of Flawil, Germany) at optimized conditions. For example, inlet air temperature of 112° C., outlet air temperature 56° C., flow rate 0.5 liters/hour are useful conditions. Particles (i.e., microspheres 62) removed from the collector are stabilized either by heat treatment in hot air (90° C. for 1 hour) or by chemical crosslinking (using 1% aqueous glutaraldehyde solution at 10:1 ratio (majority particulate solution)). The microspheres may be freeze-dried for storage.

EXAMPLE 6

Preparation of Avidinated Albumin Microspheres by Spray Drying

Mix dry albumin and dry avidin at 10:1 weight ratio (majority albumin) and add 1% aqueous glutaraldehyde solution. Heat the resulting solution at 90° C. for 15–30 minutes, then freeze dry to yield a dry powder containing a mixture of albumin and avidin. Mix the dry powder containing the mixture of albumin and avidin with the desired drug at a 2:1 weight ratio (majority mixture) and add water to yield a 1% by weight aqueous solution. Spray dry using an appropriate apparatus (for example, Model 190 spray dryer from BUCHI Laboratoriums-Technik AG of Flawil, Germany) at optimized conditions. For example, inlet air temperature of 112° C., outlet air temperature 56° C., flow rate 0.5 liters/hour are useful conditions. Particles (i.e., microspheres 62) removed from the spray dryer are stabilized either by heat treatment in hot air (for example, 90° C. for I hour) or by chemical crosslinking by mixing the particles with a 1% aqueous glutaraldehyde solution at a ratio of 1:1. The particles may be freeze-dried for storage.

EXAMPLE 7

Preparation of Biotinylated Albumin Microspheres by Coacervation

Attach biotin to albumin according to the albumin biotinylation protocol given in Example 2. Dissolve drug and albumin in water (5:1 ratio of albumin:drug by weight) to form 5% by weight solution. Add an equal volume of acetone to form microspheres. The resulting solution is then heat treated at 75° C. for 30 minutes to stabilize the particles. The particles are then washed and centrifuged. The particles are then re-suspended in water and freeze-dried.

EXAMPLE 8

Biotinylation of Poly (dl Lactide-co-glyolide) Microspheres by Spray Drying

In this example, biotinylated poly(DL lactide-co-Glycolide) (PLG) microsphere are prepared by spray drying. First, biotinylate PLG using photoactivatable biotin as described under Example 1. Mix PLG and drug at a weight ratio of 2:1, and dilute the resulting mixture in water to obtain a 1% by weight aqueous solution. Spray dry the solution using a spray dryer (for example, Model 190 spray dryer from BUCHI Laboratoriums-Technik AG of Flawil, Germany) at optimized conditions. For example, inlet air temperature of 112° C., outlet air temperature 56° C., flow rate 0.5 liters/hour are useful conditions. The particles (i.e., microspheres 62) are then removed from the collector.

EXAMPLE 9

Preparation of Biotinylated Liposomes

To prepare the liposomes containing the vasoconstrictor, the vasoconstrictor is suspended in soybean oil (Procter & Gamble, Cincinnati, Ohio) at a concentration of 30 mg/mL and blended at 12,000 rpm using a Silverson Homogenizer (Silverson Machines Ltd., of Waterside, England) for 2 minutes. Suspend phospholipids (e.g., a mixture available from Avanti Polar Lipids, Alabaster, Alabama; 82 mole % dipalmitoylphosphatidylserine, 10 mole % dipalmitoylphosphatidic acid, and 8 mole % dipalmitoylphosphitidylethanolamine-PEG 5000) (lipid concentration=5 mg/mL) in an aqueous solution comprising 8 parts by volume normal saline, 1 part propylene glycol (Fisher Chemical Co., Fairlawn, N.J.), and 1 part glycerol (Fisher Chemical Co., Fairlawn, N.J.), with 5 mg/mL of L61 Pluronic (Spectrum Laboratories Inc., Gardena, Calif.).

Add the vasoconstrictor-soybean oil suspension to the phospholipid suspension at a 1:1 volume ratio (final volume 2.0 mL) in 2-mL glass Wheaton vials. Exchange the headspace of the vials with perfluorobutane gas. Seal the vials. Agitate the sealed vials using a CAPMIX shaker (ESPE, Seefeld, Germany) for 60 seconds at 4200 rpm. The resulting suspension will contain liposomes containing the vasoconstrictor.

To attach biotin to the liposomes, dissolve 3.3 mg of the NHS ester of biotin in 130 $\mu$L of a 2:1 (volume/volume) chloroform-methanol mixture. Add 3.9 mg of liposomes to the biotin solution. Add 1.5 $\mu$L of triethylamine to 8.5 $\mu$L of chloroform and add this solution to the PS-NHS-biotin solution. Allow the reaction to proceed for two hours at room temperature. The biotinylated liposomes can be purified by high pressure liquid chromatography (HPLC).

EXAMPLE 10

Preparation of Gas-filled Biotinylated Liposomes

To prepare gas-filled liposomes containing the vasoconstrictor, the vasoconstrictor is suspended in soybean oil (Procter & Gamble, Cincinnati, Ohio) at a concentration of 30 mg/mL and blended at 12,000 rpm using a Silverson Homogenizer (Silverson Machines Ltd., of Waterside, England) for 2 minutes. Suspend phospholipids (e.g., a mixture available from Avanti Polar Lipids, Alabaster, Alabama; 82 mole % dipalmitoylphosphatidylserine, 10 mole % dipalmitoylphosphatidic acid, and 8 mole % dipalmitoylphosphitidylethanolamine-PEG 5000) (lipid concentration=5 mg/mL) in an aqueous solution comprising 8 parts by volume normal saline, 1 part propylene glycol (Fisher Chemical Co., Fairlawn, N.J.), and 1 part glycerol (Fisher Chemical Co., Fairlawn, N.J.), with 5 mg/m L61 Pluronic (Spectrum Laboratories, Inc., Gardena, Calif.).

Add the vasoconstrictor-soybean oil suspension to the phospholipid suspension at a 1:1 volume ratio (final volume=2.0 mL) in 2-mL glass Wheaton vials. Seal the vials.

Agitate the sealed vials using a CAPMIX shaker (ESPE, Seefeld, Germany) for 60 seconds at 4200 rpm. The resulting suspension will contain liposomes containing the vasoconstrictor.

To attach biotin to the liposomes, dissolve 3.3 mg of the NHS ester of biotin in 130 $\mu$L of a 2:1 (volume/volume) chloroform-methanol mixture. Add 3.9 mg of liposomes to the biotin solution. Add 1.5 $\mu$L of triethylamine to 8.5 $\mu$L of chloroform and acid this solution to the PS-NHS-biotin solution. Allow the reaction to proceed for two hours at room temperature. The biotinylated liposomes can be purified by high pressure liquid chromatography (HPLC).

While the particular embodiments of the present invention have been shown and described, practitioners will appreciate that changes and modifications can be made without departing from this invention in its broader aspect. For example, the microspheres described may be composed of substances such as proteins, lipids; carbohydrates or synthetic polymers. The microspheres can have the vasoconstrictor impregnated therein and/or coated thereon. The microspheres can release the vasoconstrictor at or near the target vessel as a result of several processes, including, but not limited to, diffusion, degradation, application of an ultrasound signal, dissolution, and chemical reaction. Therefore, the appended claims are to encompass within their scope all such changes and modifications as fall within the scope of this invention.

What is claimed is:

1. A method for treating ischemia in a patient, the method comprising:

depositing a layer of polymer on the luminal surface of a target vessel; and injecting microspheres containing a vasoconstrictor into the patient, wherein the microspheres are adapted to attach to the layer of polymer and release the vasoconstrictor in situ adjacent to the layer of polymer.

2. The method of claim 1, wherein the vasoconstrictor is administered to the target vessel for a period of time between thirty seconds and two minutes, at least four times a day, for at least 5 days.

3. The method of claim 1, wherein the vasoconstrictor is selected from the group consisting of epinephrine, norepinephrine, lysine vasopressin, 8-arginine vasopressin, angiotensin II, methoxamine hydrochloride, and analogs thereof.

4. The method of claim 1, wherein the layer of polymer and the microspheres include first members of an affinity pair; and further comprising injecting receptor molecules into the patient, the receptor molecules comprising second members of the affinity pair, wherein the second members of the receptor molecules are adapted to engage the first members of the layer of polymer and the microspheres so that the microspheres attach to the layer of polymer.

5. The method of claim 4, wherein the first member of the affinity pair is selected from the group consisting of biotin and analogs thereof and further wherein the second member of the affinity pair is selected from the group consisting of avidin and analogs thereof.

6. The method of claim 1, wherein the layer of polymer includes first members of an affinity pair, and the microspheres include second members of an affinity pair.

7. The method of claim 1, wherein the first members of the affinity pair are selected from the group consisting of biotin and analogs thereof and the second members of the affinity pair are selected from the group consisting of avidin and analogs thereof.

8. The method of claim 1, further comprising:

providing energy from an external energy source to rupture the microspheres, thereby releasing the vasoconstrictor.

9. The method of claim 8, wherein the energy is an ultrasound beam.

10. The method of claim 1, wherein the microspheres are comprised of a material selected from the group consisting of poly(DL Lactide-co-Glycolide), poly-lactic acid, polyglycolic acid, gelatin, polyester, alginate, polyethylene oxide, lipid, gas-filled liposomes, and albumin.

11. The method of claim 1, wherein the layer of polymer is selected from the group consisting of poly-lactic acid, poly-glycolic acid, polyphosphazenes, polyhydroxybutyric acid, poly-caprolactone, polyanhydrides, polyethylene glycol, and copolymers and mixtures thereof.

12. The method of claim 1, wherein the layer of polymer is deposited using a stent.

13. The method of claim 1, wherein the layer of polymer is deposited by paving the endoluminal surface of the target vessel with a hydrogel.

14. The method of claim 1, wherein the polymer or microspheres are biotinylated using photoactivatable biotin.

15. The method of claim 1, wherein the act of depositing a polymer comprises applying a hydrogel precursory to the target vessel and causing the polymerization of the precursor to form the layer.

* * * * *

UNITED STATES PATENT AND TRADEMARK OFFICE
CERTIFICATE OF CORRECTION

PATENT NO. : 6,544,543 B1
DATED : April 8, 2003
INVENTOR(S) : Evgenia Mandrusov, Christopher J. Buchko and Wouter E. Roorda It is certified that error appears in the above-identified patent and that said Letters Patent is hereby corrected as shown below:

<u>Column 18,</u>
Line 9, change "claim 1" to -- claim 6 --.

Signed and Sealed this

Twelfth Day of August, 2003

JAMES E. ROGAN
*Director of the United States Patent and Trademark Office*